United States Patent [19]
Guentzler

[11] Patent Number: 5,373,728
[45] Date of Patent: Dec. 20, 1994

[54] GALVANIC ANODE DEVICE AND ELECTROLYSIS CONTROL MONITOR

[76] Inventor: William D. Guentzler, 454 Goulburn Ct., El Cajon, Calif. 92020

[21] Appl. No.: 92,077
[22] Filed: Jul. 16, 1993
[51] Int. Cl.⁵ .............. G01N 17/04; G01R 27/08; G08B 5/24
[52] U.S. Cl. ............................ 73/40.7; 73/86; 204/197; 204/404; 422/53; 324/71.2; 324/71.1
[58] Field of Search ........... 73/40.7, 86; 204/404; 422/53; 324/71.2, 71.1; 116/206

[56] References Cited

U.S. PATENT DOCUMENTS

| | | | |
|---|---|---|---|
| 4,090,170 | 5/1978 | Lincklaen-Arriens et al. | 340/5 R |
| 4,101,828 | 7/1978 | Dehler et al. | 324/71.2 |
| 4,202,750 | 5/1980 | Khoury | 204/197 |
| 4,514,730 | 4/1985 | Ming | 422/53 |
| 4,516,069 | 5/1985 | Schmanski | 324/71.2 |
| 4,839,580 | 6/1989 | Moore et al. | 324/65 R |
| 4,863,571 | 9/1989 | Chambaere | 204/404 |
| 4,915,910 | 4/1990 | Manning et al. | 422/53 |
| 5,171,524 | 12/1992 | Niolon | 422/53 |
| 5,243,298 | 9/1993 | Runner | 324/71.2 |

Primary Examiner—Hezron E. Williams
Assistant Examiner—J. David Wiggins
Attorney, Agent, or Firm—John K. Donaghy

[57] ABSTRACT

The use of a sacrificial anode in a plumbing system or in the cooling system of an internal combustion engine or the like to protect the system against the destructive effects of electrolysis caused by the many different metals employed in modern plumbing systems or engines is disclosed, along with several methods and apparatus for monitoring the condition of the sacrificial anode to indicate when replacement is needed for continued protection of the system. Physical, optical and electrical systems are taught, each designed to indicate the need for replacement of the anode in an easily discernable manner.

12 Claims, 4 Drawing Sheets

GALVANIC ANODE DEVICE AND ELECTROLYSIS CONTROL MONITOR

BACKGROUND OF THE INVENTION

Modern internal combustion engine designers employ a wide variety of metals in engine construction in order to obtain the best combination of light weight and performance. These metals may include aluminum and its alloys for water pumps and cylinder heads, brass for thermostats, copper/brass alloys or aluminum for radiators, cast iron for engine blocks or aluminum engine blocks with steel cylinder sleeves. When these diverse metals are combined in an internal combustion engine with a liquid cooling system, electrolysis is generated which erodes these different engine parts, causing early failure of many parts and necessitating expensive repairs.

Similarly, electrolysis and the corrosion which accompanies it is found in residential and industrial plumbing systems, again due to the many various metals which may be used for pipes, faucets, valve cartridges or the like. As in the cooling system of an internal combustion engine, these metals are electrically coupled by the liquid in the system, and electrolysis and corrosion may occur at any time.

In the past, especially in the marine industry, the most common method of dealing with undesired, destructive electrolysis was to install a sacrificial anode on the device (boat hull or outboard engine lower drive unit) to be protected from electrolysis. The sacrificial anode is formed from a metal, such as zinc, which will be attacked by electrolysis more readily than the material of the protected device, so that the anode is "sacrificed" to save the protected object. Usually, sacrificial anodes are easily replaced to facilitate their removal when used up and replacement with fresh elements for continued protection.

BRIEF DESCRIPTION OF THE INVENTION

It is an object of this invention to utilize a sacrificial anode in the cooling system of a modern internal combustion engine or dynamometer absorption unit, in an industrial or residential plumbing system, or any liquid-filled system which includes a plurality of dissimilar metals to control electrolysis within the protected system and avoid costly repairs or premature part failure. It has been discovered that a magnesium or magnesium alloy anode works best to protect a plumbing system or an engine with a cooling system whichemploys fresh Water or ethylene glycol coolant liquids, while a zinc or zinc alloy anode works best in marine applications employing salt water as a coolant liquid. In either case, the use of a galvanic anode as a sacrificial anode stops erosion of valuable metallic parts and restricts material erosion exclusively to the anode, which may be easily and inexpensively replaced when it is expended.

A sacrificial anode may also be used in residential or commercial water systems to control internal erosion and corrosion of pipes, valves and faucets.

Another object of this invention is to provide an effective way of monitoring the condition of a sacrificial anode so that it can be replaced when needed so as to provide continuous protection for the object or system on which protection is desired. Once a sacrificial anode is completely eroded due to electrolysis, its beneficial effects stop, and electrolysis will begin to attack the protected object. Several different monitoring means are set forth in the body of this specification.

DETAILED DESCRIPTION OF THE PREFERRED EMBODIMENTS

Like numerals in the several drawing figures denote like elements throughout this specification.

This galvanic anode device is designed to protect the various metal parts of residential or industrial plumbing systems, internal combustion engines, dynamometer absorption units or marine engines from the destructive effects of electrolysis by serving as a sacrificial anode, and includes a variety of methods for determining when the anode needs to be replaced in order to maintain continuous protection.

The anode may be formed of either magnesium or zinc alloy in accordance with the following percentages:

| | |
|---|---|
| cadmium | .025–.150% |
| copper | .005% max. |
| iron | .005% max. |
| lead | .006% max. |
| silicon | .125% max. |
| aluminum | .100–.500% |
| zinc or magnesium | remainder |

It has been discovered that the magnesium alloy performs best in fresh water and ethylene glycol coolant, and the zinc alloy performs best in salt water, as required for some marine applications.

The electrolysis control monitoring aspects of the invention are quite important, since once the anode is completely sacrificed, all protection is lost. Therefore, it is imperative that the sacrificed anode be replaced immediately upon its destruction, and an indicator of its condition will aid in this replacement.

Figure 1A:
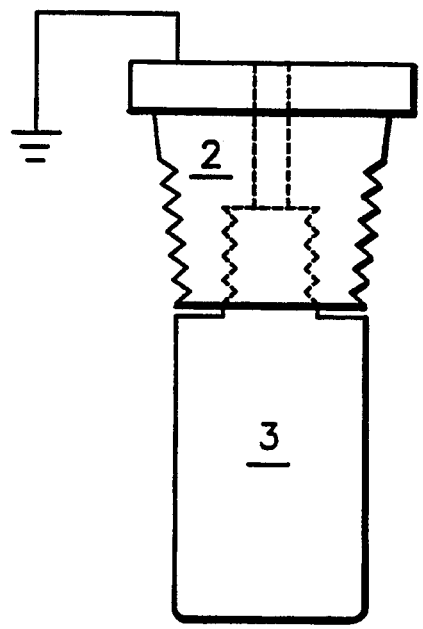
FIGS. 1A, 1B and 1C show the mechanical, pressure-operated embodiments of the electrolysis control monitor of the invention.
Figure 1B:
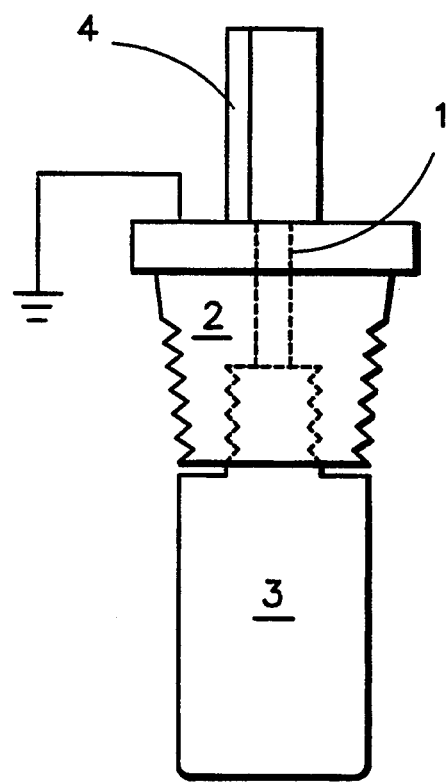
Figure 1C:
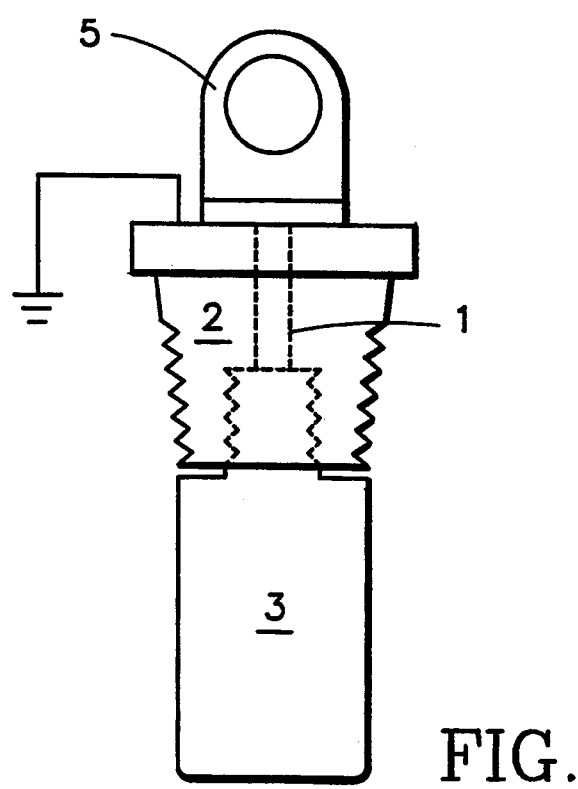

The simplest indicators are mechanical in nature, and require no maintenance for their operation. Referring to FIGS. 1A, 1B and 1C, since most internal combustion engine cooling systems are operated under pressure at nominally fifteen pounds per square inch, and most plumbing systems are also maintained under pressure, a small hole 1 drilled through the mounting plug 2 for the sacrificial anode 3 will, upon destruction of the anode 3 by electrolysis, cause a small leak to indicate that the anode 3 needs replacement. Alternatively, a small test strip 4 of litmus paper or the like as shown in FIG. 1B might be placed adjacent the through-hole 1, with the litmus paper changing color when contacted by the leaking fluid to indicate anode destruction. A third version, FIG. 1C, adds a small rotatable indicator 5, sometimes called a toro-wink, at the outside end of the through-hole 1. This indicator 5 will change color when exposed to the fluid pressure following destruction of the anode 3, thus giving a ready signal of the need for replacement while preventing the small leak.

Figure 2A:
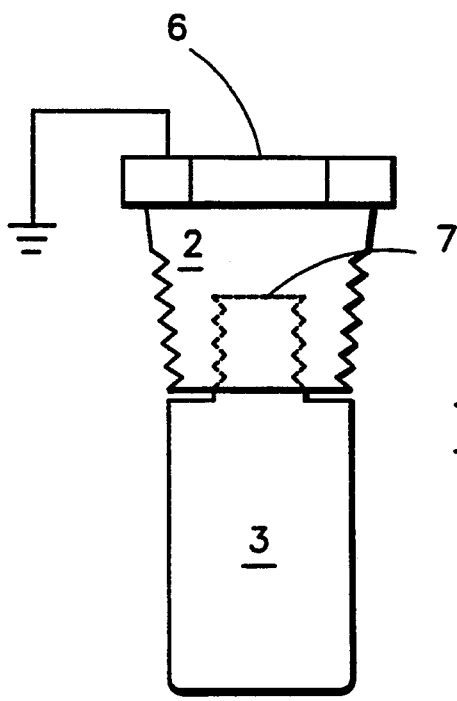
FIGS. 2A and 2B illustrate the optical embodiments of the electrolysis control monitor of the invention.
Figure 2B:
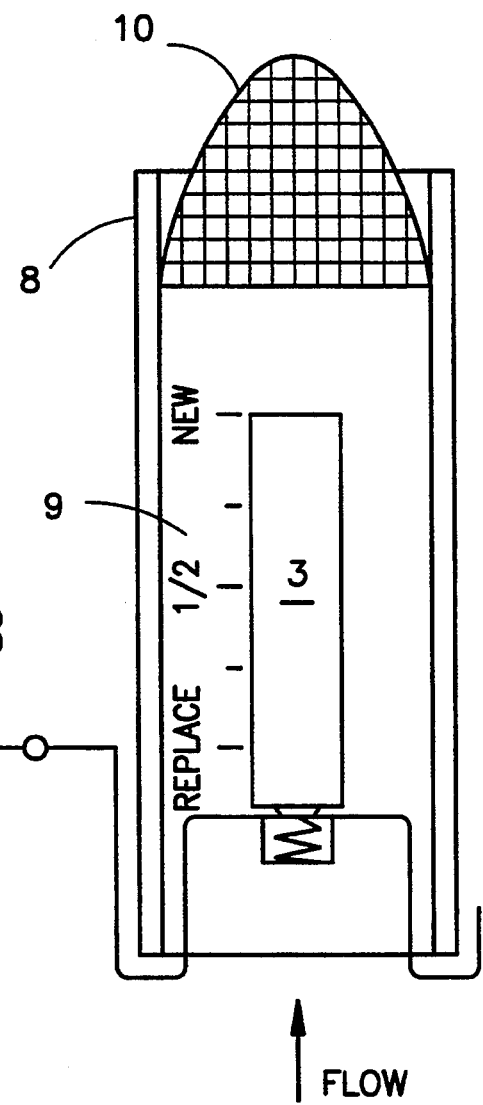

Referring to FIGS. 2A and 2B, optical indicator systems are also maintenance-free. The simplest form of this indicator, shown in FIG. 2A, utilizes a sight glass 6 on the end of the anode mounting plug 2 and a colored dot 7 on the end of the anode 3 which is mounted in the plug 2. Destruction of the anode 3 will destroy the colored dot 7 also, and the sight color viewed through the glass 6 will change to the color of the fluid in the system. A second optical indicator, FIG. 2B, provides in-line positioning of the anode 3 in a clear plastic tube 8, with a wear scale 9 imprinted or engraved on the tube 8 to indicate the amount of anode which still remains. Optionally a wire mesh strainer 10 may be added to this embodiment.

Figure 3A:
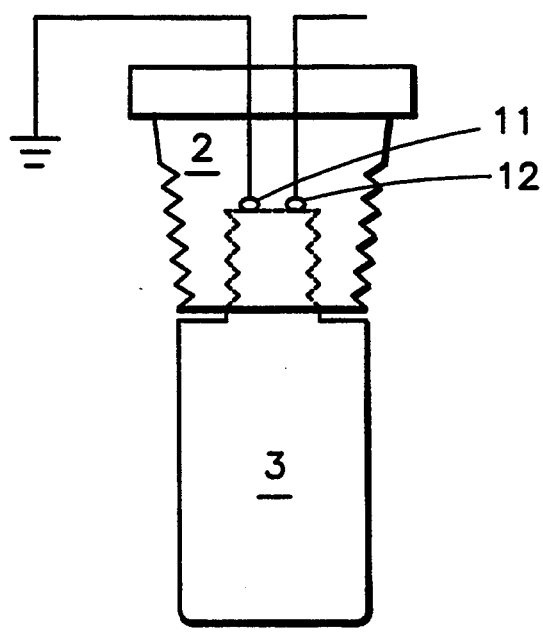
FIGS. 3A and 3B are directed to the basic electrical embodiments of the electrolysis control monitor of the invention.
Figure 3B:
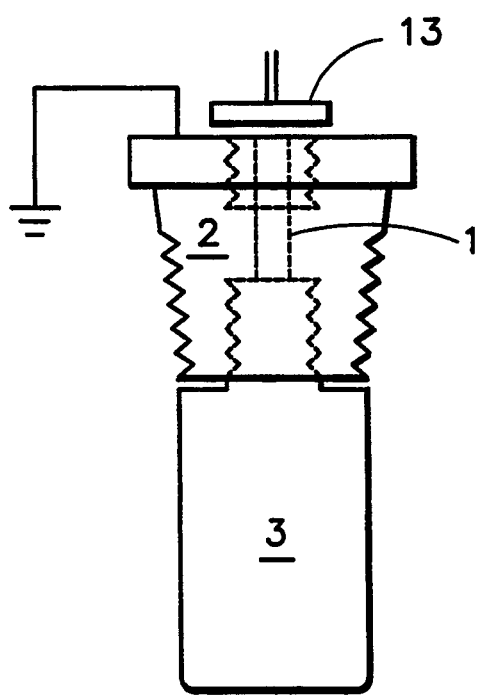

Electrical electrolysis control monitoring systems are the most complex and sophisticated of the indicators, but they are also perhaps the best, since a variety of audible, visible and tactile alarms can be provided to draw attention to a sacrificed anode, unlike the passive systems noted above which require observation of the indicator for recognition of the condition which needs to be corrected. A basic electrical indicator may use the anode material to close an electrical circuit as shown in FIG. 3A, in which the anode 3 provides a closed circuit between electrical contacts 11 and 12 mounted in anode mounting plug 2. Destruction of the anode 3 will open the circuit between contacts 11 and 12 and sound an alarm. Another basic electrical indicator, FIG. 3B, provides a pressure sensor 13 at the outside end of a through-hole 1 in the anode mounting plug 2. When the anode 3 is destroyed, pressure from the fluid system is applied to the pressure sensor 13 to generate an electrical signal which is used to initiate an alarm.

Figure 4:
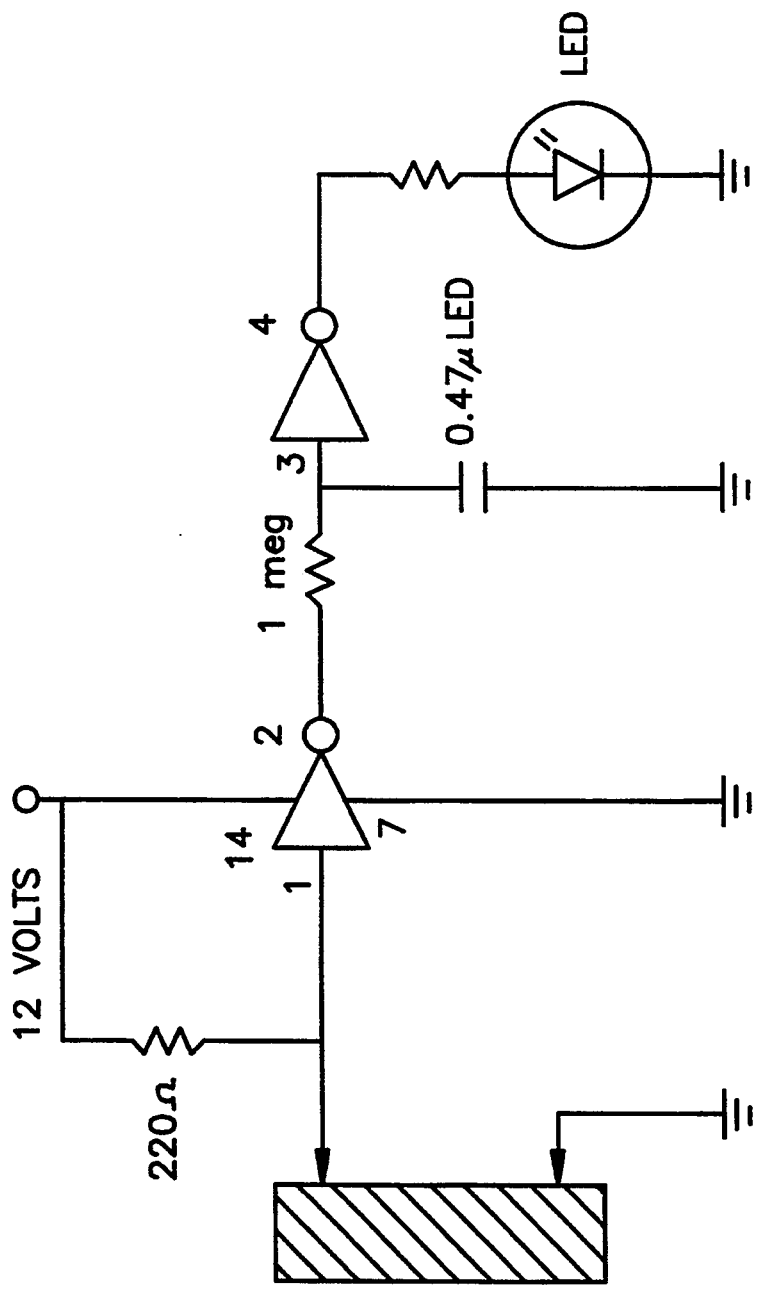
FIG. 4 shows an electrical schematic for providing a visual alarm in combination with the embodiments of FIGS. 2A and 3B.

The circuit schematic shown in FIG. 4 is exemplary of the type which might be used with an electrical indicator such as those shown in FIGS. 3A and 3B to provide an alarm indication of a sacrificed anode.

Any combination of these indicators may, of course, be used, with the redundancy serving to assure a definite indication of the condition of the anode. For example, an electrical indicator can be mounted in a clear plastic tube having a wear scale imprinted thereon, and the tube may also have a through-hole drilled into the anode mount, thus providing combined mechanical, optical and electrical indicators.

I claim:

1. In a replaceable sacrificial anode system for protection against electrolysis of an internal combustion engine pressurized cooling system having a means for monitoring the condition of said anode, and thus the condition of said electrolysis protection system, such that a visual indication is given upon destruction of said anode to indicate that replacement is necessary for continued protection of said cooling system and its elements, an aperture is formed through the mounting plug for said sacrificial anode, such that destruction of said anode will cause a small leak to occur through aperture in said cooling system.

2. In a replaceable sacrificial anode system for protection against electrolysis of a pressurized residential or industrial plumbing system having a means for monitoring the condition of said anode, and thus the condition of said electrolysis protection system, such that a visual indication is given upon destruction of said anode to indicate that replacement is necessary for continued protection of said plumbing system and its elements, an aperture is formed through the mounting plug for said sacrificial anode, such that destruction of said anode will cause a small leak to occur through aperture in said plumbing system.

3. In the sacrificial anode system of claim 1, a chemical indicator paper placed over said leaking aperture to provide a positive indication by reaction with said leak of said leak.

4. In the sacrificial anode system of claim 1, a rotatable mechanical indicator placed over said leaking aperture, the pressure of said leak causing a positive indication of said leak by rotating said indicator within a fixed mounting face.

5. In the sacrificial anode system of claim 1, a mounting plug for said replaceable anode having a transparent viewing port through said plug to said anode, and a colored portion on the end of said anode, the gradual destruction of which will cause a change in the color viewed through said port.

6. In the sacrificial anode system of claim 1, said anode being mounted within a transparent flow passage of said cooling system, such that destruction of said anode is readily discernable by observation through said transparent passage.

7. In the sacrificial anode system of claim 1, a pressure transducer placed over said leaking aperture, such that the increase in pressure sensed at said leak will cause said transducer to generate a signal which can be utilized to cause an indicator or alarm to be initialized, thereby indicating the need to replace said anode.

8. In the sacrificial anode system of claim 2, a chemical indicator paper placed over said leaking aperture to provide a positive indication by means of reaction with said leak of said leak.

9. In the sacrificial anode system of claim 2, a rotatable mechanical indicator placed over said leaking aperture, the pressure of said leak causing a positive indication of said leak by rotating said indicator within a fixed mounting base.

10. In the sacrificial anode system of claim 2, a mounting plug for said replaceable anode having a transparent viewing port through said plug to said anode, an a colored portion on the end of said anode mounted in said plug, such that destruction of said anode will cause a change in the color viewed through said port.

11. In the sacrificial anode system of claim 2, said anode being mounted within a transparent flow passage of said plumbing system, such that destruction of said anode is readily discernable by observation through said transparent passage.

12. In the sacrificial anode system of claim 2, a pressure transducer placed over said leaking aperture, such that the increase in pressure sensed at said leak will cause said transducer to generate a signal which can be utilized to cause an indicator or alarm to be initialized, thereby indicating the need to replace said anode.

* * * * *